United States Patent
Tayebi

(10) Patent No.: US 8,276,830 B1
(45) Date of Patent: Oct. 2, 2012

(54) NO LEAKAGE OR DRIPPING AIR-SCENTING DEVICE

(76) Inventor: Amad Tayebi, Westford, MA (US)

( * ) Notice: Subject to any disclaimer, the term of this patent is extended or adjusted under 35 U.S.C. 154(b) by 573 days.

(21) Appl. No.: 12/462,367

(22) Filed: Aug. 1, 2009

Related U.S. Application Data

(60) Provisional application No. 61/188,858, filed on Aug. 13, 2008.

(51) Int. Cl.
*A24F 25/00* (2006.01)
(52) U.S. Cl. .......................................... 239/44; 239/45
(58) Field of Classification Search .............. 239/42–45, 239/47, 51.5, 53, 55–57, 34
See application file for complete search history.

(56) References Cited

U.S. PATENT DOCUMENTS

| | | | | |
|---|---|---|---|---|
| 4,165,835 A * | 8/1979 | Dearling | ..................... | 239/51.5 |
| 4,352,457 A * | 10/1982 | Weick | ............................. | 239/45 |
| 4,739,928 A * | 4/1988 | O'Neil | ............................ | 239/45 |
| 4,915,301 A * | 4/1990 | Munteanu | ...................... | 239/45 |
| 2008/0217426 A1* | 9/2008 | Brown et al. | ................... | 239/45 |

* cited by examiner

*Primary Examiner* — Davis Hwu
(74) *Attorney, Agent, or Firm* — American Patent Associates; Amad Tayebi

(57) ABSTRACT

An air-scenting device, which can be mounted vertically, horizontally or at any orientation, including upside down, without any leakage or dripping is disclosed in which there is no free-to-flow fluid under gravitational force, thus causing no spillage at any orientation. The device comprises a barrel containing an open-cell porous mass which contains air-scenting liquid within its pores and a porous wick surrounded by a cage, having perforations, and allowing evaporation of air-scenting fluid transferred to it by capillary action.

5 Claims, 1 Drawing Sheet

U.S. Patent                Oct. 2, 2012                US 8,276,830 B1
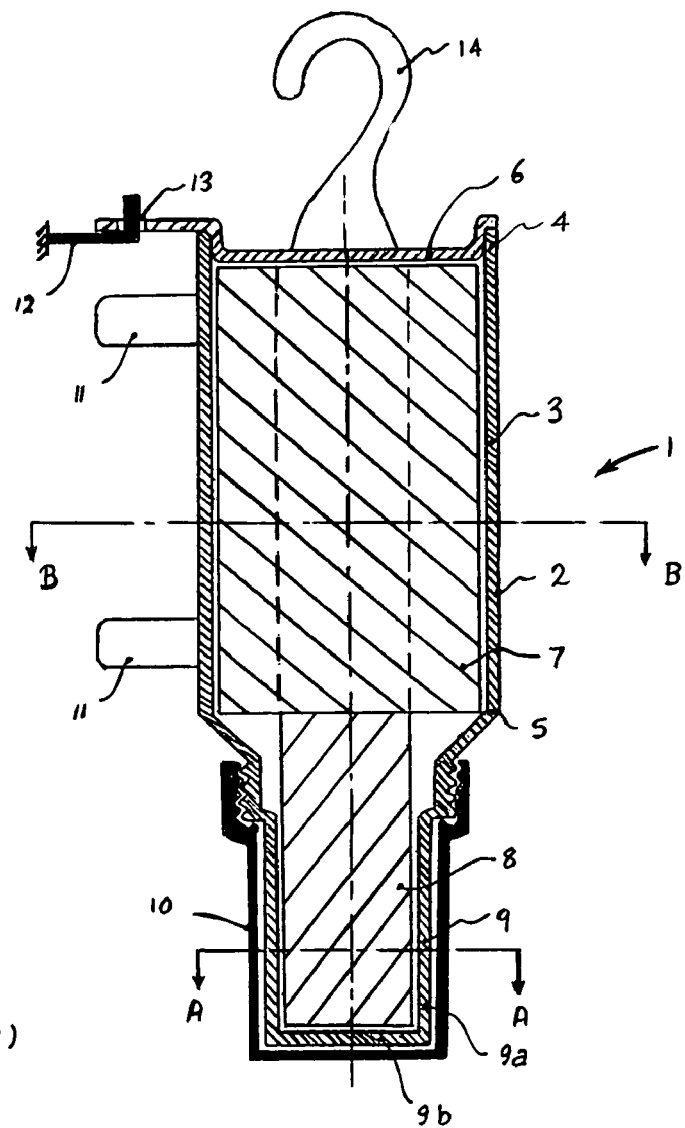
(Fig. 1)
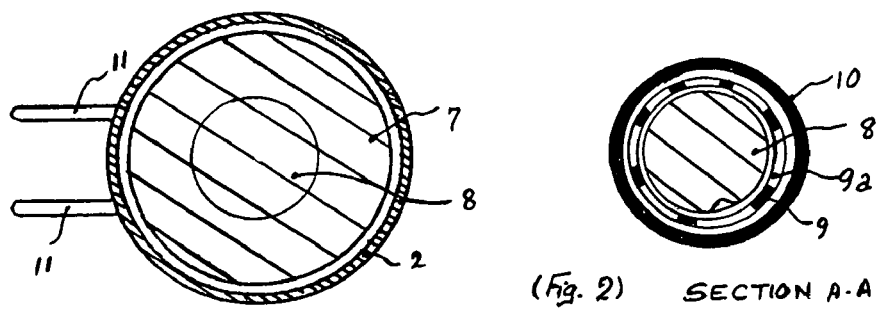
(Fig. 3) SECTION B-B
(Fig. 2) SECTION A-A

NO LEAKAGE OR DRIPPING AIR-SCENTING DEVICE

STATEMENT REGARDING A RELATED PROVISIONAL PATENT APPLICATION

This utility patent application claims priority of a related provisional patent application filed on Aug. 13, 2008, Ser. No. 61/188,858, titled Apparatus and Method for Scenting Air and submitted by the same applicant, This provisional patent application is incorporated in this application, in its entirety, by reference. Also, a copy of this provisional patent application is attached to this application.

FIELD OF THE INVENTION

The present invention is in the field of air-scenting devices. In particular it is directed to an air-scenting device which is safer to use by preventing inadvertent contact between the fingers of the user of the air-scenting device and the wick containing the air-scenting liquid.

BACKGROUND OF THE INVENTION

Typical air-scenting devices of the prior art comprise a container which contains an air-scenting liquid The air-scenting liquid has a free surface and a depth. The air-scenting liquid may be water-based, oil-based, solvent-based and/or containing a mixture of water, oil and/or solvent. The air scenting device also includes a wick having one end immersed in the air-scenting liquid and the other end above the liquid free surface.

In accordance with the present invention a wick is defined as a permeable porous mass through which a fluid moves by capillary action and wicking is defined as movement or transfer of fluid within a permeable porous mass caused solely by capillary action.

In air-scenting devices of the prior art, air-scenting liquid moves, by capillary action, through the wick, against gravitational force and evaporates into surrounding area thereby scenting the surrounding air. Optionally, a heater may be used to increase the rate of evaporation of the air-scenting fluid.

Some of the drawbacks of the prior art are 1) spillage and/or leakage of the air-scenting liquid when its container is tilted or damaged and 2) inadvertent contact of the wick by the hand or skin of the user. The air-scenting device of the present invention overcomes these drawbacks and is therefore, child-resistant. It can be mounted vertically, horizontally or at any orientation, including upside down, without any leakage or dripping. It also shields all wetted components so that inadvertent contact with skin of the user is prevented.

BRIEF DESCRIPTION OF THE DRAWINGS

FIG. 1 shows a longitudinal section of the air-scenting device of the of the present invention.

FIG. 2 shows a cross-sectional view of the air-scenting device of the present invention, at location A-A.

FIG. 3 shows a cross-sectional view of the air-scenting device of the present invention, at location B-B.

DETAILED DESCRIPTION OF PREFERRED EMBODIMENTS OF THE INVENTION

FIG. 1 shows a longitudinal sectional view of child-resistant air-scenting device 1, in accordance with the present invention. As shown therein, it comprises a hollow barrel 2. Barrel 2 may be in the form of a hollow prism, circular, triangular, square, rectangular or polygonal tubing. Barrel 2 has a middle portion 3, a distal end 4 and a proximal end 5. Middle portion 3 is impermeable to flow of fluids. In accordance with the present invention, the term fluid includes liquids, gases and vapors.

Barrel 2 contains a fluid reservoir 7. Fluid reservoir 7 is in the form of a porous open-cell mass. An open-cell mass is defined as a mass containing hollow open pores through which fluids may flow through the mass by capillary action and/or as a result of pressure drop in the direction of flow. Reservoir 7 may be made of cohesively or adhesively bonded particles, sintered particles, paper tissue, fibrous material, open-cell polymeric foam, bonded or unbonded nonwoven sheet material or any other porous open-cell material known in the art.

The open-cell mass of reservoir 7 contains an air-scenting fluid 20 (not shown in the drawing) within at least a portion of its open cells. Optionally, open cell mass of reservoir 7 may be made of a material that also absorbs the same air-scenting fluid. In its preferred embodiment, in accordance with the present invention, and therefore, no chipping action may result the open-cell mass of reservoir 7 is not surrounded by any free-to-flow fluid by orienting barrel 2 in any direction, including horizontally, vertically (upright, or upside down) or at any other inclination.

Open-cell mass of reservoir 7 has a first capillary rise (CR1). In accordance with the present invention, the capillary rise (CR) of an open-cell mass or a wick is defined as the maximum vertical height reached by a fluid solely due to wicking action (also known as capillary effect) of the porous mass or the wick having one of its ends dipped into a container containing a fluid and measured from the surface of the fluid. The capillary rise (CR) of an open-cell mass or a wick, as defined in accordance with present invention, may be increased by using surfactants, increasing the density (mass per unit volume) and/or decreasing the particle or fiber size of the open-cell mass or the wick. Also, in accordance with the present invention, when two open-cell masses, an open-cell mass and a wick or two wicks, having different capillary rises, are brought into contact with one another, fluid contained within the open cells of the lower capillary rise open-cell mass or wick is transferred, by capillary action or effect, to the open cells of the open-cell mass or wick with the higher capillary rise.

Distal end 4 is closed with a distal end cover 6. Cover 6 is preferably impermeable to fluids. In other embodiments of the present invention, cover 6 may have perforations.

Proximal end 5 is attached to an air-permeable protective cage 9. Cage 9 has a side wall 9a and an end portion 9b. Side wall 9a has perforations which may be of a circular, triangular, elongated, diamond, square, rectangular or polygonal shape. Cage end portion 9b may also have similar perforations. In accordance with the present invention, perforations in side wall 9a and end portion 9b are sufficiently small such that the fingers of a user handling device 1 may not inadvertently come into contact with an air-scenting porous plug, open-cell mass or wick 8 contained within the interior of cage 9. Many air-scenting fluids, presently used in air-scenting devices, cause skin irritation upon contact. As such, by restricting and/or preventing inadvertent contact between the fingers of a user handling device 1 and wick 8, the air-scenting device of the of the present invention is safer to handle than those of the prior art.

Proximal end 5 and protective cage 9 may be permanently or detachably attached. They may also be made of the same or different materials. They may also be monolithically made, for example by injection or blow molding as one integral component.

Porous plug, open-cell mass or wick 8, contained within cage 9, has a capillary rise (CR2) and at least a portion of its surface is in contact with at least a portion of the surface of open-cell mass of reservoir 7. In accordance with the present invention, capillary rise 0112 is at least equal to capillary rise CR1. Thus, as the air-scenting fluid evaporates from wick 8, air-scenting fluid continues to flow from open-cell mass of reservoir 7 into wick 8. Preferably, in accordance with the present invention, capillary rise CR2 is higher than capillary rise CR1, thus causing wick 8 to drain the open-cell mass of reservoir 7 completely and provide a full utilization of the air-scenting fluid initially injected or contained within the open-cell mass of reservoir 7.

Alternatively, open-cell mass of reservoir 7 and wick may be monolithically-made, being or forming one integral component or a monolithically-made wick. Such an alternative design, is easier to manufacture and offers lower production costs. In this design, as the air-scenting fluid evaporates from the portion of the monolithically-made wick contained in cage 9, fluid continues to flow, through capillary action, from the portion of the monolithically-made wick contained within middle portion 3 into the portion contained within cage 9 until the entire monolithically-made wick is dried.

In accordance with the present invention, the cross-sectional area, shape and length of wick 8 and open-cell mass of reservoir 7 may be equal, unequal, similar or dissimilar.

Prior to use of device 1, cage 9 is covered by proximal end cap or cover 10. Cap 10 may be a threaded cap, a press-fit cap or a snap-fit cap. It may also be monolithically-made with and integrally attached to cage 9 or middle portion 3.

Optionally, barrel 2 may have mounting hanging or suspension means. A preferred mounting means is shown in FIG. 1 as nonconductive plug prongs 11 which may be inserted into an electric wall outlet having similarly-shaped receiving openings, Alternatively, a suspension or hanging hook 14, may be attached at or to the distal end 4 of barrel 2 or to distal end cover 6. Prongs 11 and barrel 2 may be monolithically-made or monolithically combined as one integral component, for example by injection molding. Hanging hook 14 and distal end 4 and/or distal end cover 6 may also be monolithically-made or monolithically combined as one integral component, for example by injection molding. Distal end cover 6 or distal end 4 of barrel 2 may also be adapted to have hanging hook receiving hole(s) 13 designed for suspending air-scenting device 1 from hanging hook 12.

FIG. 2 shows a cross-sectional view of air-scenting device 1 at location A-A and FIG. 3 shows a cross-sectional view of air-scenting device 1 at location B-B.

The invention claimed is:

1. An air-scenting device, which can be mounted vertically, horizontally or at any orientation, including upside down, without any leakage or dripping, during its operational state, comprising:
    a hollow barrel, said barrel having a middle portion, a distal end and a proximal end, said middle portion being impermeable to flow of fluids, said barrel containing a fluid reservoir, said fluid reservoir being in the form of an open-cell porous mass, said mass containing an air-scenting liquid within a portion of its open cells,
    the entire said open-cell mass of said reservoir being not surrounded by any free-to-flow, under gravitational action, fluid and having a first capillary rise, said distal end being closed with a distal end cover,
    said proximal end being attached to an air permeable protective cage,
    said cage having a side wall, and an end portion and containing, within its interior, an air-scenting porous wick, said side wall having perforations,
    said wick having at least a portion of its surface in contact with at least a portion of surface of said mass, said wick having a second capillary rise,
    said cage side wall and end portion encapsulating said wick and allowing air flow around said wick.

2. The air-scenting device of claim 1 wherein said proximal end and said protective cage being permanently attached.

3. The air-scenting device of claim 1 wherein said proximal end and said protective cage being detachably attached.

4. The air-scenting device of claim 1 wherein said open-cell mass and said wick being monolithically made.

5. The air-scenting device of claim 1 wherein said barrel having mounting means, said mounting means being nonconductive plug prongs which may be inserted into an electric wall outlet having similarly-shaped receiving openings.

* * * * *